United States Patent [19]

Thorne

[11] 4,154,795
[45] May 15, 1979

[54] MICROTEST PLATES

[75] Inventor: Anthony C. Thorne, Bordage, Guernsey, Channel Islands

[73] Assignee: Dynatech Holdings Limited, St. Peter Port, Guernsey, Channel Islands

[21] Appl. No.: 817,748

[22] Filed: Jul. 21, 1977

[30] Foreign Application Priority Data

Jul. 23, 1976 [DE] Fed. Rep. of Germany ....... 2633283
Dec. 16, 1976 [GB] United Kingdom ............... 52653/76

[51] Int. Cl.² .......................... B01L 3/00; B01L 9/00; C12B 1/00; C12K 1/10
[52] U.S. Cl. ..................................... 422/99; 195/127; 206/460; 206/562; 211/74; 220/23.2; 220/23.4; 220/23.6; 220/23.8; 422/102
[58] Field of Search .......................... 23/292, 259 US; 195/127, 140; 206/460, 558, 562; 220/23.2, 23.4, 23.6, 23.8; 211/74 US

[56] References Cited

U.S. PATENT DOCUMENTS

| 3,415,361 | 12/1968 | Adams, Jr. et al. ........ 23/253 R UX |
| 3,441,383 | 4/1969 | Moore et al. ........................... 23/292 |
| 3,504,376 | 3/1970 | Bednar et al. ..................... 23/292 X |
| 3,540,858 | 11/1970 | Rochte et al. ........................... 23/292 |
| 3,649,462 | 3/1972 | Jessup ................................. 23/259 X |
| 3,649,464 | 3/1972 | Freeman ............................ 23/292 X |
| 3,682,597 | 8/1972 | Husch .................................... 23/259 |
| 3,724,654 | 4/1973 | Gerard et al. ..................... 23/292 X |
| 3,759,374 | 9/1973 | Helger et al. ..................... 206/459 X |
| 3,778,232 | 12/1973 | McMorrow, Jr. ................. 23/259 X |
| 3,907,505 | 9/1975 | Beall et al. ......................... 23/292 X |
| 4,038,149 | 7/1977 | Liner et al. ........................... 195/127 |

FOREIGN PATENT DOCUMENTS 2051581  5/1972  Fed. Rep. of Germany ............. 23/292
 758517 10/1956  United Kingdom ............ 220/DIG. 15

*Primary Examiner*—Joseph Scovronek
*Attorney, Agent, or Firm*—Strauch, Nolan, Neale, Nies & Kurz

[57] ABSTRACT

A microtest plate is characterized by a tray conveniently moulded of foam plastics, having a multiplicity of compartments and a multiplicity of individual wells fitted into the compartments, at least some of the wells preferably being moulded integrally with one another, and preferably being arranged in one or more rows.

11 Claims, 16 Drawing Figures

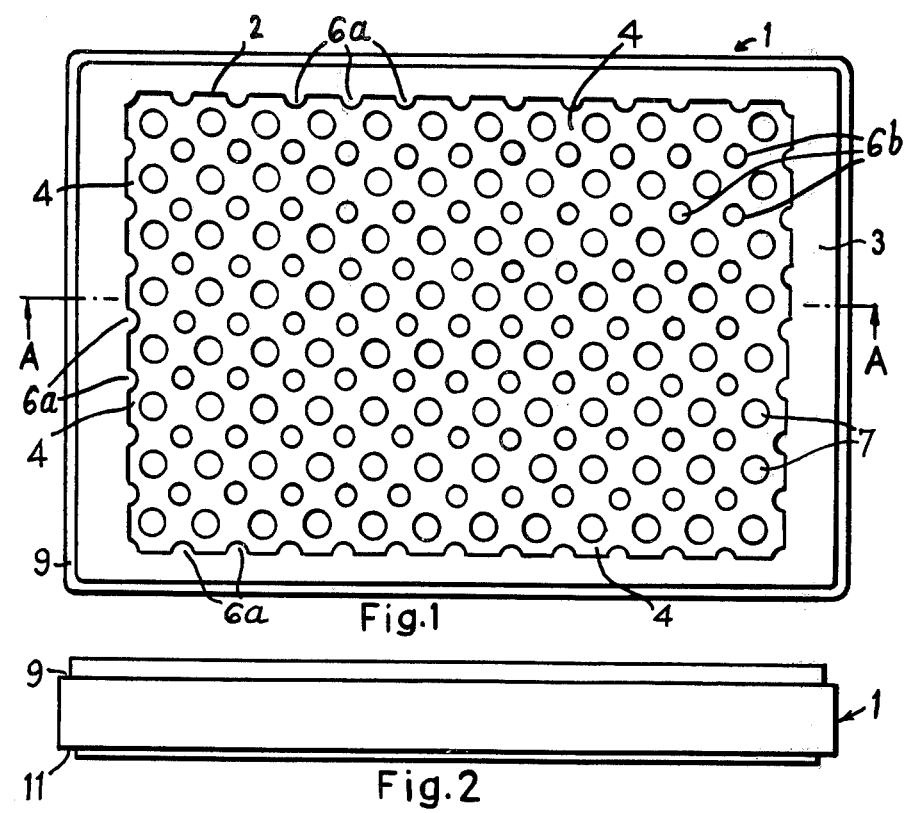
Fig.1
Fig.2
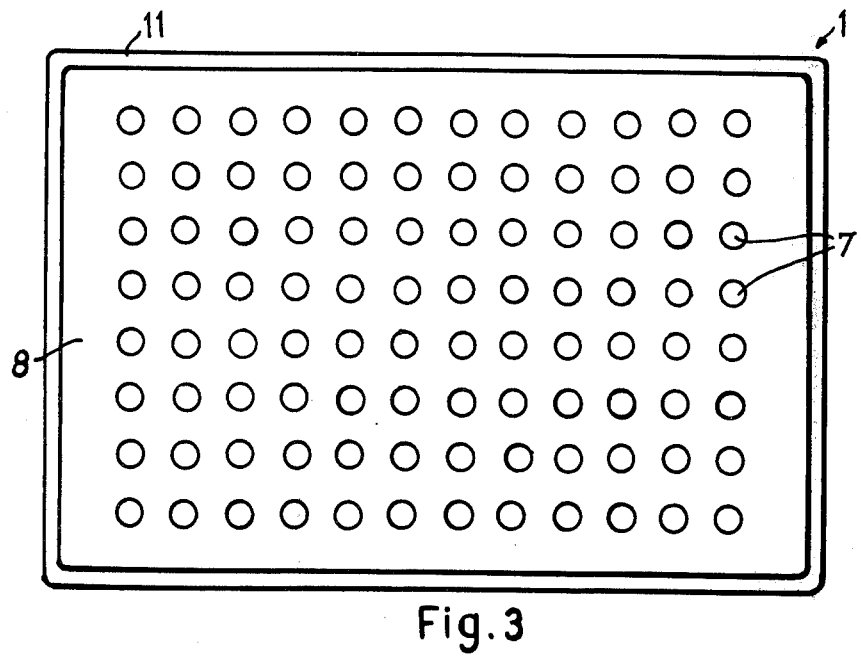
Fig.3

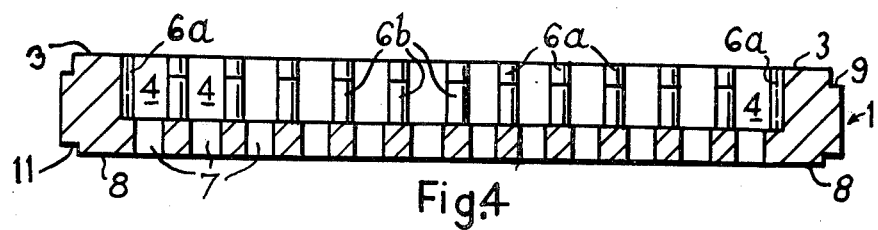
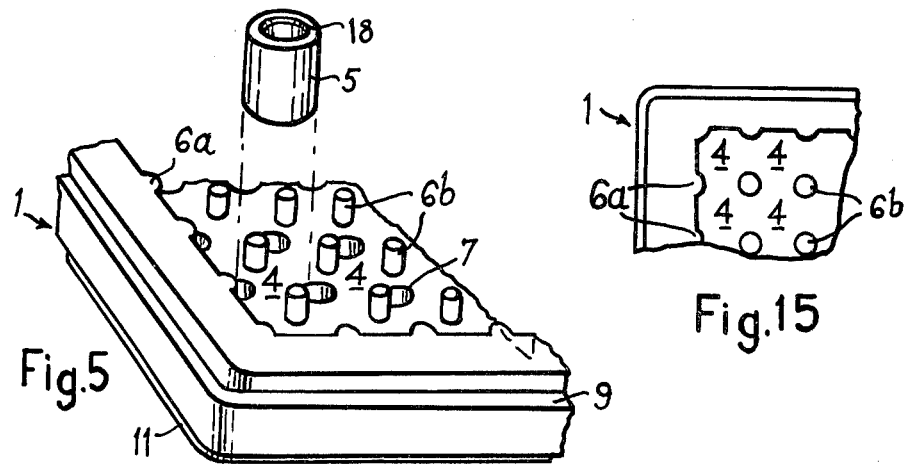
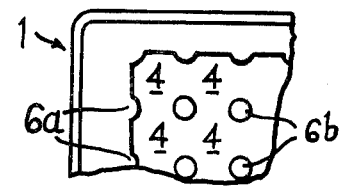
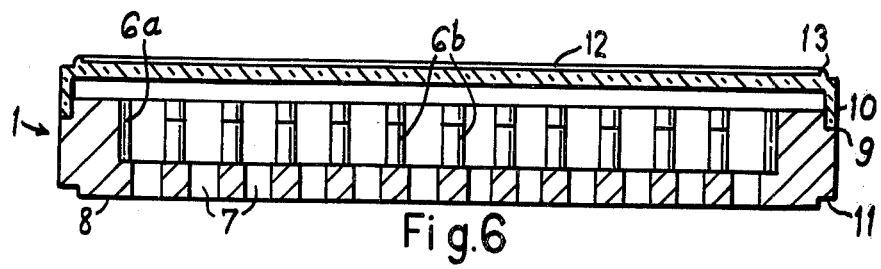
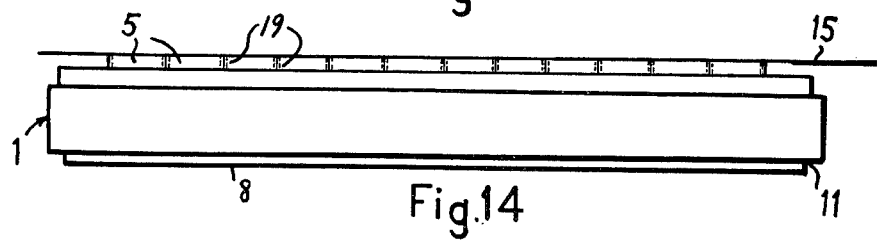

MICROTEST PLATES

BACKGROUND OF THE INVENTION

1. Field of the Invention

This invention relates to laboratory apparatus for use in the conducting of body fluid investigations such as complement fixation tests, hemagglutinition tests, hemagglutinition inhibition tests and metabolic inhibition tests and immuno chemical and both isotopic and non-isotopic immuno assays. More particularly the invention relates to a microtest or microtitration plate.

In the known microtitration plates the wells, cups or recesses for receiving samples of the body fluid to be tested are formed by drilling or moulding. For example, U.S. Pat. No. 3,356,462 discloses a moulded microtitration plate made of a transparent rigid synthetic plastics material and having twelve rows of integral open-top wells or cups, eight in each row. The main disadvantage of such microtitration plates is their lack of versatility and expense due to the integral cups or wells.

Accordingly, it is an object of the present invention to provide a microtest plate which has a greater degree of versatility.

SUMMARY OF THE INVENTION

This object is achieved in accordance with the present invention by providing a microtest plate which is characterised by a tray, conveniently moulded from foam plastics, having a plurality of compartments and by a multiplicity of individual wells fitted into the compartments. The compartments are preferably arranged in one or more rows and/or columns.

One advantage of the present invention resides in the fact that the wells can be pretreated with different test materials for testing different diseases in any desired combination in one tray since the pretreatment can be carried out before the wells are fitted in the tray. For example, the wells can be pretreated with a wetting agent or processed to enable them to grow cell cultures. In another example with different concentrated antigen, antibody, or antibiotic test materials, as well as with radio-isotopes for use in radio-immuno-assay and enzyme linked test materials for use in enzyme linked immuno-sorbent assays for the determination of the antigen or antibody content of body fluids. The pretreated wells can then be pre-processed, for example by freeze drying the test material and the processed wells fitted into the tray compartments in the desired combination. The individual wells can then easily be covered or sealed by any suitable means. Thus, a single tray can be used to perform a variety of tests on a body fluid sample from a single patient.

As a further advantage of the invention the individual wells enable the tray to be made of a less expensive material than that of the wells, thereby decreasing its expense as compared with those microtitration plates with integral wells and the cost of replacing said plates if they are disposed of as is usually the case.

In order to facilitate assembly of the trays and wells and removal of the wells from the tray compartments, preferably at least some of the wells are moulded integrally with one another. For example, the wells may be integrally connected together by means of stems, webs, strips or the like of moulding material such as mould flashings, extending between the individual wells and enabling the wells to be separated from one another if required. By this means the wells may be more easily manipulated and more rapidly fitted into and removed from the compartments.

The wells may be integrally moulded in any convenient formation, for example one or more lines or rows connected together in a strip, or a block of wells.

Preferably, the bottoms of the compartments of the tray have apertures therethrough. Thus, when the wells are provided with optical quality flat bases as is preferred optical and colour readings may be taken of the samples of these wells through the bottom of the tray so that the samples do not have to be removed from the wells for analysis by optical or colorimetry techniques. Moreover, the apertures in the compartment bottoms enable the wells to be readily removed individually, or together where some of the wells are integrally connected, from the tray, merely by pushing them out through the apertures.

Alternatively, the wells may be removed from the top of the tray by means of tweezers, for example when the tray has no apertures, and to assist in such removal the tops of the walls conveniently project beyond the upper surface of the tray.

In a preferred embodiment of the invention, the compartments are defined by rows and columns of posts upstanding from the tray. Such a construction lends itself readily to moulding. Conveniently, the outermost posts are half posts which are integral with the side walls of the tray recess and the inner posts are preferably of lesser height than the outermost posts.

The wells may be sealed by an adhesive cover strip or individual plugs. Preferably, the adhesive cover strip has perforations around the wells so that the wells remain sealed when the cover strip is removed and can be individually opened as required. A similar advantage can be achieved if the plugs are carried by a cover strip having perforations around the plugs. The cover strip is conveniently made from sterilizable polyester adhesive sealing tape.

Instead of or in addition to the sealing strip or plugs the microtitration plate may comprise a lid which fits into a rebate on the tray and clears the tops of the wells.

The wells are conveniently made of a material having an affinity for molecules of the body fluid sample or material with which the sample may be mixed for testing and analysis. For example the walls may be made of rigid PVC or polystyrene which have the advantage of having an ability to attract protein molecules but any other suitable plastics material which has an affinity for sample or test molecules may be used.

BRIEF DESCRIPTION OF THE DRAWINGS

FIG. 1 is a plan view of one form of tray forming one part of a microtitation plate constructed in accordance with the invention, FIGS. 2 and 3 are side and underneath plan views respectively of the tray of FIG. 1, FIG. 4 is a cross-section on the line A—A of FIG. 1 looking in the direction of the arrows, FIG. 5 is a fragmentary perspective view of the tray of FIG. 1 showing the manner in which one of a multiplicity of individual wells forming the other part of the plate is fitted in the tray, FIG. 6 is a cross-section showing the tray with a lid thereon, FIG. 11 is a side view of the plate of FIG. 7 with the lid thereon, FIG. 14 is a side view of the plate of FIG. 7 showing the tray with a cover strip instead of a lid.

FIG. 15 is a fragmentary plan view of a modified form of tray, and

DESCRIPTION OF PREFERRED EMBODIMENTS

Figure 7:
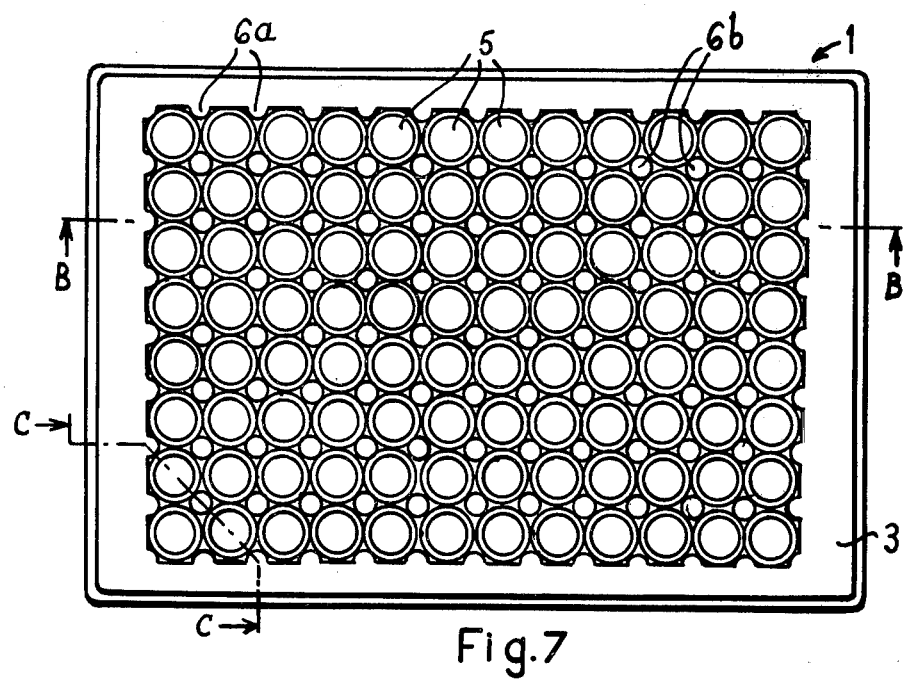
FIGS. 7 and 8 are plan and side views respectively of the microtitration plate showing the wells fitted in the tray.

Referring to FIGS. 1 to 6, there is shown a tray 1, made of polystyrene foam, having a tray recess 2, upper surface 3 and an undersurface 8. The tray recess 2 has compartments 4 arranged in twelve rows with eight compartments in each row and defined by rows and columns of posts upstanding from the base of the recess. In the compartments 4 can be fitted a multiplicity of individual rigid micro-test tubes or wells, of which one well 5 is shown in FIG. 5, for receiving a sample of a patient's body fluid to be tested, the sample usually being mixed with test material in the wells. The outermost posts 6a are half posts which are integral with the side walls of the recess 2 and extend to the height of the recess to be flush with the upper surface 3 of the tray whereas the inner posts 6b are of lesser height than the outer posts 6a.

The bottom of each compartment 4 has an aperture 7 extending therethrough to enable optical or colour readings to be taken of the sample in the well 5 without removing the sample from the well and to permit the wells to be removed by pushing them out through the apertures. The upper surface 3 of the tray has a rebate 9 into which fits a lid 10 (FIG. 6) which covers the compartments 4 and surface 3. The tray 1 also has a rebate 11 in its undersurface 8 so that the under surface 8 can fit into a depression 12 in the upper surface of the lid 10 with the rebate 11 engaging a lip 13 of the lid of a similar tray for stacking one tray upon the other.

Figure 8:
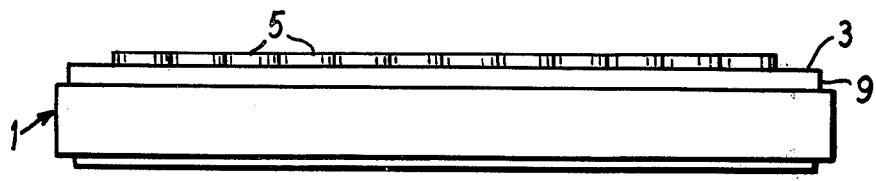
Figure 9:
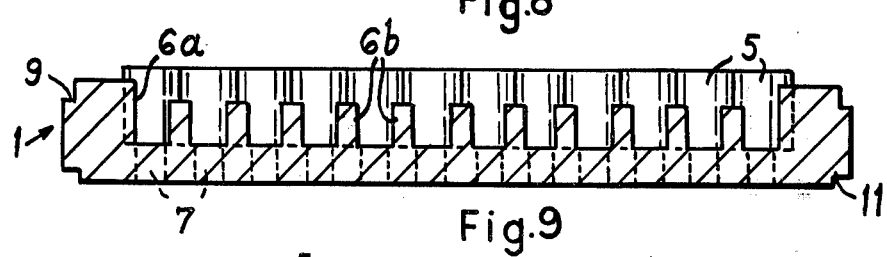
FIG. 9 is a cross-section on the line B—B of FIG. 7.
Figures 10, 12:
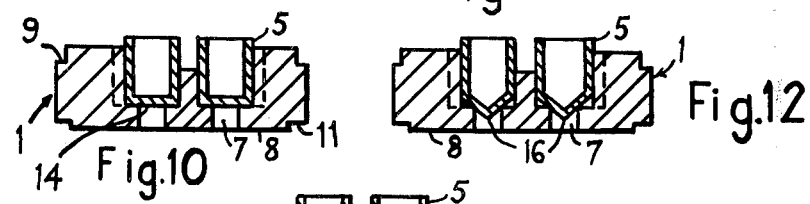
FIG. 10 is a cross-section on the line C—C of FIG. 7, showing one shape of well base.
FIGS. 12 and 13 are views similar to that of FIG. 10 but showing two further shapes of well base.

As will be apparent from FIGS. 7 to 9, the wells 5 fit into the compartments 4 with their cylindrical outer surfaces each engaging four posts of a respective compartment. The wells which are of rigid transparent PVC or polystyrene have a frusto-conical top inner edge portion as indicated at 18 in FIG. 5 and project beyond the upper surface 3 of the plate 1 to facilitate removal of the individual wells with tweezers from the top of the tray. As shown in FIG. 10 each well 5 has a flat optical quality base 14.

Figure 14A:
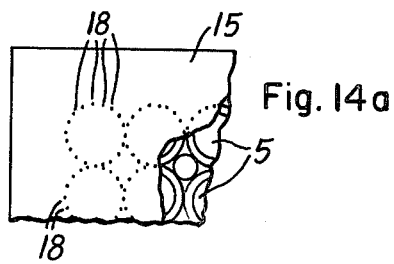
FIG. 14a is a scrap top plan view of FIG. 14.

Instead of or in addition to the lid 10 which as shown in FIG. 11 clears the tops of the wells, an adhesive sealing cover strip 15 may be applied to the tops of the wells 5 to seal them as shown in FIG. 14, conveniently with perforations 18 (FIG. 14a) around the individual wells. Preferably as shown in FIG. 14, one or more rows of wells may be sealed by a corresponding number of adhesive cover strips or by plugs 19 carried by the cover strip 15 or cover strips to seal a strip or several strips of cells.

Figure 13:
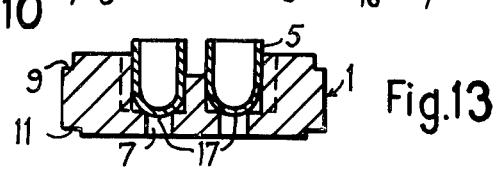

The shape of the bases of the wells may be conical as indicated at 16 in FIG. 12 or hemispherical as indicated at 17 in FIG. 13 instead of flat or any combination of wells with such bases may be fitted in the tray compartments.

In the modification shown in FIG. 15, the apertures 7 are omitted from the bottoms of the compartments 4 of the tray 1.

Figure 16:
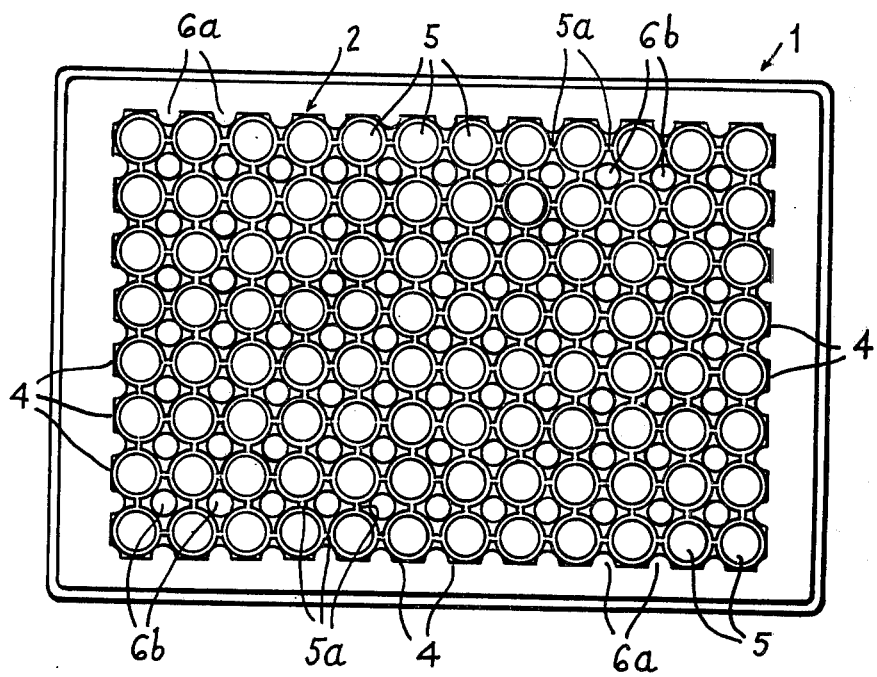
FIG. 16 is a plan view of another embodiment of microtitration plate.

The embodiment of FIG. 16 differs from the previous embodiments in that all the wells 5 are moulded integrally with one another by means of stems 5a which may be mould flashings. Thus, all the individual wells can be fitted together into the compartments of the tray recess 2 so that assembly of the tray and wells can be simply and rapidly achieved. The stems 5a may easily be broken to enable one or more wells to be separated from each other when required. Alternatively one or more rows of wells 5 may be integrally connected by means of the separable stems 5a to form a strip of wells.

Various modifications may be made without departing from the scope of the invention. For example, the tray may be moulded from flexible silicone rubber instead of foam plastics, to facilitate removal of the wells. The wells may be made of glass instead of a plastics material. Moreover, the wells may be of different heights and the tops of the wells may be flush with the upper surface 3 of the tray in which case the lower posts 6b will facilitate the removal of the wells by means of tweezers from the top of the tray.

I claim:

1. In a microtitration plate having a multiplicity of wells for containing microliter quantities of fluid samples for analysis and arranged on the plate in straight rows at right angles relative to one another, the improvement comprising means for enabling the wells to be individually removable from the plate, said means comprising a tray formed as a one piece plastics moulding, a multiplicity of discrete wells, at least some of which are moulded integrally with one another and are interconnected by stem means whereby said at least some of said wells are readily separable from one another, and means on said tray defining a multiplicity of compartments arranged in straight rows at right angles relative to one another, said discrete wells being disposed in upright positions in said compartments, and said means defining said compartments including means engaging the side walls of said wells whereby to retain said wells in said upright positions.

2. A microtitration plate as claimed in claim 1, wherein said stem means interconnect said at least some of said wells in at least one straight row to form at least one strip of wells.

3. A microtitration plate as claimed in claim 1, wherein said tray has a bottom and means defining apertures extending through said bottom substantially centrally of said compartments whereby to enable optical readings to be taken of fluid samples in said wells.

4. A microtitration plate as claimed in claim 1, wherein said means engaging said side walls of said wells comprises rows and columns of posts upstanding from said tray.

5. A microtitration plate as claimed in claim 1, wherein said tray has a peripheral wall having an upper surface and said wells have tops which project beyond said upper surface of said peripheral wall to facilitate individual removal of said wells from said tray.

6. A microtitration plate as claimed in claim 1, wherein at least some of said wells are sealed by an adhesive cover strip to seal at least a strip of wells.

7. A microtitration plate as claimed in claim 6, wherein said cover strip defines perforations therein which extend around the individual wells.

8. A microtitration plate as claimed in claim 1, wherein at least some of said wells are sealed by plugs.

9. A microtitration plate as claimed in claim 8, wherein said plugs are carried by a cover strip to seal at least a strip of wells, the cover strip defining perforations around the plugs.

10. A microtitration plate as claimed in claim 1, wherein said tray has means defining a rebate therein and said plate further comprises a lid which fits into the rebate and clears the tops of said wells.

11. A microtitration plate as claimed in claim 1, wherein:
 (a) the tray comprises a bottom and means defining a rectangular wall extending around the periphery of the bottom and defining a rectangular recess within the said wall;
 (b) said compartment defining means divides said recess into said multiplicity of compartments;
 (c) said means engaging said side walls of said wells includes a multiplicity of discrete posts projecting upwardly from the tray bottom and disposed at equally spaced positions in rows extending at right angles relative to one another;
 (d) said posts projecting upwardly from the tray bottom by a distance less than the height of said peripheral wall;
 (e) posts moulded integrally with said peripheral wall at each end of each of said rows;
 (f) each compartment is defined by four adjacent posts disposed at the corners of a square zone;
 (g) means define apertures extending through the tray bottom substantially centrally of said compartments; and
 (h) said discrete wells are moulded from plastics material and one of said wells is supported in each compartment with the bottom of the wells seated on the tray bottom.

* * * * *